United States Patent [19]

Seele et al.

[11] Patent Number: 5,290,792
[45] Date of Patent: Mar. 1, 1994

[54] AZOLYLMETHYLSPIRO(2.5)OCTANOLS AND FUNGICIDES CONTAINING THESE

[75] Inventors: Rainer Seele, Fussgoenheim; Norbert Goetz, Worms; Gisela Lorenz, Neustadt; Eberhard Ammermann, Ludwigshafen, all of Fed. Rep. of Germany

[73] Assignee: BASF Aktiengesellschaft, Ludwigshafen, Fed. Rep. of Germany

[21] Appl. No.: 771,095

[22] Filed: Oct. 4, 1991

[30] Foreign Application Priority Data

Oct. 29, 1990 [DE] Fed. Rep. of Germany ....... 4034337

[51] Int. Cl.⁵ ................. A01N 43/653; C07D 249/08
[52] U.S. Cl. ................ 514/383; 548/267.8; 548/268.6
[58] Field of Search ............ 548/267.8, 268.6; 514/383

[56] References Cited

U.S. PATENT DOCUMENTS 5,096,912  3/1992  Scherkenbeck et al. ............ 514/383
5,102,899  4/1992  Seele et al. ..................... 514/383

*Primary Examiner*—Patricia L. Morris
*Attorney, Agent, or Firm*—Oblon, Spivak, McClelland, Maier & Neustadt

[57] ABSTRACT

Azolylmethylspiro[2.5]octanols of the formula

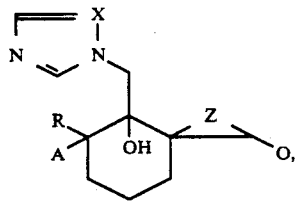

where
A and R are each hydrogen or alkyl;
D is alkyl, cycloalkyl, cycloalkenyl, biphenylyl, naphthyl, hetaryl or phenyl, it being possible for each of these radicals to be substituted;
Z is $CH_2$ or O,
X is CH or N, and the plant-compatible acid addition salts and metal complexes thereof are used as or in fungicides.

5 Claims, No Drawings

AZOLYLMETHYLSPIRO(2.5)OCTANOLS AND FUNGICIDES CONTAINING THESE

The invention relates to novel azole compounds, to processes for the preparation thereof and to fungicides containing these.

The use as fungicides of E-1-[1-(4-chlorophenyl)-1-hydroxy-2-(1,2,4-triazol-1-yl)ethyl]-2-phenylcyclopropane (EP 212,605) or 2-(4-chlorobenzylidene)-6,6-dimethyl-1-(1H-1,2,4-triazol-1-ylmethyl)-1-hexanol (EP 378,953) has been disclosed. However, the fungicidal actions are not satisfactory in all cases.

It is an object of the present invention to provide novel azole compounds with improved fungicidal actions.

We have found that this object is achieved by compounds of the formula I

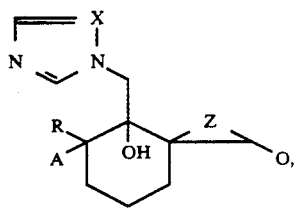

where

A and R are each hydrogen or $C_1$–$C_4$-alkyl;
D is $C_1$–$C_8$-alkyl, $C_3$–$C_6$-cycloalkyl, $C_5$–$C_8$-cycloalkenyl, biphenylyl, naphthyl, hetaryl or phenyl, it being possible for each of these radicals to be substituted once to three times by halogen, nitro, phenoxy, amino, $C_1$–$C_4$-alkyl, $C_1$–$C_4$-alkoxy or $C_1$–$C_4$-haloalkyl;
Z is $CH_2$ or O, and
X is CH or N, and the plant-compatible acid addition salts and metal complexes thereof.

The present invention also relates to processes for preparing the novel compounds, to intermediates used for this, to fungicidal agents which contain the novel azolylmethylcyclohexanols as active substances, and to methods for controlling fungi using these compounds.

The azolylmethylcyclohexanols of the formula I are generally obtained in the form of racemates or diastereomer mixtures. These isomers can be separated and isolated in pure form in a conventional manner, for example on the basis of their solubility or of that of their salts or else by column chromatography. Pure enantiomers can be obtained by conventional methods from diastereomers isolated in this way.

The present invention relates both to the individual diastereomers or enantiomers and to the mixtures resulting from the synthesis and to the fungicides containing these.

Preferred azolylmethylcyclohexanols I are those where D is $C_1$–$C_8$-alkyl, preferably -alkyl, especially methyl, ethyl, n-propyl, isopropyl, n-butyl, sec-butyl and tertbutyl; preferred alkyl radicals with more than 4 carbon atoms are n-pentyl and neopentyl;

phenyl and halophenyls such as 2-chlorophenyl, 3-chlorophenyl, 4-chlorophenyl, 2-fluorophenyl, 3-fluorophenyl, 4-fluorophenyl and 2-bromophenyl, 3-bromophenyl and 4-bromophenyl, 2,3-dichlorophenyl, 2,4-dichlorophenyl, 2,5-dichlorophenyl and 2,6-dichlorophenyl, and 2-chloro-4-fluorophenyl and 2-chloro-6-fluorophenyl;

phenyl monosubstituted by nitro, phenoxy, amino and $C_1$–$C_4$-alkyl, such as 3-nitrophenyl, 4-nitrophenyl, 3-phenoxyphenyl, 4-phenoxyphenyl, 3-aminophenyl and 4-aminophenyl, and 4-ethylphenyl, 4-isopropylphenyl and 4-tert-butylphenyl;

phenyl substituted by two or three of the abovementioned but different radicals, such as 2-chloro-6-methylphenyl; phenyl substituted once or twice by $C_1$–$C_4$-alkoxy, such as 2-methoxyphenyl, 3-methoxyphenyl, 4-methoxyphenyl, 4-tert-butoxyphenyl and 2,4-dimethoxyphenyl, and 3,4-dimethoxyphenyl;

trihalomethylphenyls such as 2-trifluoromethyl-, 3-trifluoromethyl- and 4-trifluoromethylphenyl;

p-biphenylyl;

1-naphthyl and 2-naphthyl;

hetaryl with 5 or 6 ring atoms, particularly 6-membered rings with up to three nitrogen atoms, such as 2-pyridyl, 3-pyridyl and 4-pyridyl, and 5-membered rings with preferably one or two O, S or N atoms, especially 2-furyl, 2-thienyl, 3-thienyl, 4-oxazolyl, 4-thiazolyl, 4-isoxazolyl, 5-isoxazolyl and 5-imidazolyl;

$C_3$–$C_6$-cycloalkyl, preferably cyclopentyl and cyclohexyl, $C_5$–$C_8$-cycloalkenyl, preferably 3-cyclohexenyl.

A and R can be identical or different and each is preferably hydrogen or n-alkyl of 1 to 4 carbon atoms, especially methyl.

Suitable acid addition salts are the plant compatible salts of those acids which do not impair the fungicidal action of I, e.g. the hydrochlorides, bromides, sulfates, nitrates, phosphates, oxalates and dodecylbenzenesulfonates. However, since the activity of the salts derives from the cation, the anion is generally immaterial. The novel active ingredient salts are expediently prepared by reacting the azolylmethylcyclohexanols (I) with suitable acids.

Metal complexes of the novel compounds I or their salts are preferably formed with metals of group II such as magnesium or calcium, of group IIIA or IVa such as aluminum, tin or lead, or of group Ib to VIIB and VIII, with the elements of the first transition series being particularly preferred, especially copper, zinc, manganese, iron, cobalt and nickel. The azolylmethylcycloalkanols are reacted with appropriate metal salts for this purpose.

The compounds of the formula I can be prepared by reacting a compound of the formula II

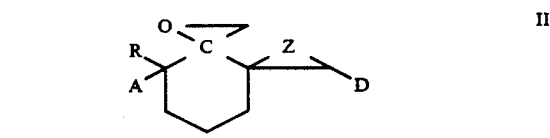

in which A, R, D and Z have the abovementioned meanings, with a compound of the formula III

in which Me is hydrogen or a metal atom and X is CH or N. Preferred compounds III are those where Me is hydrogen or an alkali metal atom, especially sodium or potassium.

If Me is hydrogen, the ratio of III:II is expediently from 2:1 to 6:1, especially about 3:1, by weight.

The reaction is carried out in the presence or absence of a solvent or diluent, expediently with the addition of an inorganic or organic base and with or without the addition of a reaction promoter. Preferred solvents and diluents include ketones such as acetone, methyl ethyl ketone or cyclohexanone, nitriles such as acetonitrile or propionitrile, alcohols such as methanol, ethanol, isopropanol, n-butanol or glycol, esters such as ethyl acetate, methyl acetate or butyl acetate, ethers such as tetrahydrofuran, diethyl ether, dimethoxyethane, dioxane or diisopropyl ether, amides such as dimethylformamide, dimethylacetamide or N-methylpyrrolidone, sulfolane or mixtures thereof.

Examples of suitable bases, which may also be used as acid acceptors in the reaction, are alkali metal hydroxides such as lithium, sodium or potassium hydroxide, alkali metal carbonates such as sodium or potassium carbonate or sodium or potassium bicarbonate, pyridine or 4-dimethylaminopyridine. However, it is also possible to use other customary bases.

Preferred reaction promoters are metal halides such as sodium iodide or potassium iodide, quaternary ammonium salts such as tetrabutylammonium chloride, bromide or iodide, or crown ethers such as 12-crown-4, 15-crown-5, 18-crown-6 or dicyclohexano-18-crown-6.

The reaction is generally carried out at from 20° to 120° C., and at atmospheric or superatmospheric pressure, continuously or batchwise.

If Me is a metal atom, the preferred ratio III:II is from 1:1 to 3:1, in particular 1:1, by weight. The reaction is carried out in the presence or absence of a solvent or diluent and with or without the addition of an inorganic or organic base. The preferred solvents and diluents include amides such as dimethylformamide, diethylformamide, dimethylacetamide, N-methylpyrrolidone, hexamethylphosphoric triamide, sulfoxides such as dimethyl sulfoxide, and sulfolane.

Examples of suitable bases, which may also be used as acid acceptors in the reaction, are alkali metal hydrides such as lithium, sodium and potassium hydride, alkali metal amides such as sodium and potassium amide, and sodium or potassium tert-butylate.

The reaction is generally carried out at from −10° to 120° C., preferably at from 20° to 80° C. When a solvent is present the reaction is expediently carried out at the boiling point thereof.

The starting compounds II can be prepared by conventional methods in a straightforward manner from the ketones of the formula IV

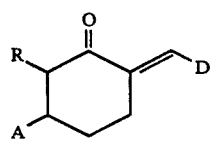

e.g. by reaction with trimethylsulfoxonium iodide (cf. Corey, Chaykovsky, J. Am. Chem. Soc. 64 (1962) 3782).

The compounds IV can be prepared by conventional methods of olefin synthesis (Houben-Weyl-Muller,
Methoden der organischen Chemie, Georg Thieme Verlag, Stuttgart, 1972, Vol. V, 1b).

Examples of compounds II are listed in Table 1.

The compounds of the formula I and the salts and metal complexes thereof are suitable as fungicides, being well tolerated by plants.

PREPARATION EXAMPLES

I. Preparation of the starting materials

Method 1

2-(4-Trifluoromethylbenzylidene)cyclohexanone

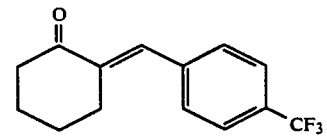

6 g of nickel acetylacetonate are added to 530 g (5.4 mol) of cyclohexanone and the mixture is refluxed for 10 minutes. Then 157 g (0.9 mol) of 4-trifluoromethylbenzaldehyde are slowly added dropwise, and the mixture is refluxed with a water trap. The reaction mixture is then concentrated, and the residue is distilled under reduced pressure, 75 g (33%) of product being obtained at 114° C. (0.25 mbar).

Method 2

1-Oxa-5-(4-trifluoromethylphenyl)dispiro[2.0.2.4]decane

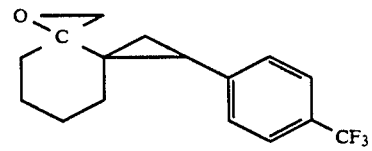

24 g of 2-(4-trifluoromethylbenzylidene)cyclohexanone are dissolved in 100 ml of N,N-dimethylformamide and, at 0° C. under a nitrogen atmosphere, 41.6 g (0.19 mol) of trimethylsulfoxonium iodide are added.

Then 22 g of potassium tert-butylate are rapidly added and the mixture is heated to 60° C. After the reaction mixture has been stirred at 60° C. for three days, 100 ml of water are added to the solution and the mixture is extracted several times with methyl tert-butyl ether. The isolated organic phase is washed twice with water, dried over sodium sulfate and concentrated, resulting in 21.2 g (80%) of product.

II. Preparation of the final products

EXAMPLE 1

4-(1,2,4-Triazol-1-ylmethyl)-4-hydroxy-1-(4-trifluoromethylphenyl)spiro[2.5]octane.

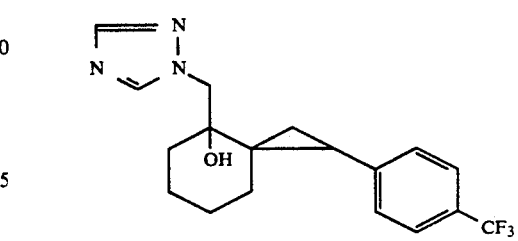

21 g of sodium hydroxide solution (50% by weight) are added to a solution of 18.2 g (0.26 mol) of 1,2,4-triazole in 100 ml of N,N-dimethylformamide, and the mixture is heated at 50° C. for 30 minutes. Then, at room temperature, 21 g (0.07 mol) of 1-oxa-5-(4-trifluoromethylphenyl)dispiro[2.0.2.4]octane dissolved in 50 ml of N,N-dimethylformamide are added dropwise. After the reaction mixture has been stirred at room temperature (20° C.) for 15 hours, 100 ml of water are added to the solution and it is extracted with methyl tert-butyl ether several times. The isolated organic phase is washed twice with water, dried over sodium sulfate and concentrated. Crystallization of the residue from methyl tert-butyl ether/n-hexane results in the product as a mixture of enantiomers.

Yield: 2.1 g (8%)

Melting point: 120°14 126° C.

The compounds listed in Table 2 can be prepared in a manner corresponding to Example 1.

TABLE 1

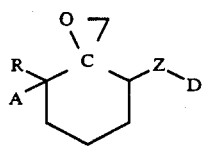

| Ex | A | R | D | Z | $^1$H-NMR/Melting point |
|---|---|---|---|---|---|
| 1 | H | H | 4-CF$_3$—C$_6$H$_4$ | CH$_2$ | 2.84 (dd) |
| 2 | H | H | 4-CF$_3$—C$_6$H$_4$ | O | |
| 3 | H | CH$_3$ | 4-CF$_3$—C$_6$H$_4$ | CH$_2$ | |
| 4 | CH$_3$ | CH$_3$ | 4-CF$_3$—C$_6$H$_4$ | CH$_2$ | |
| 5 | CH$_3$ | CH$_3$ | 4-CF$_3$—C$_6$H$_4$ | O | |
| 6 | H | H | C$_6$H$_5$ | CH$_2$ | |
| 7 | H | H | C$_6$H$_5$ | O | |
| 8 | CH$_3$ | CH$_3$ | C$_6$H$_5$ | CH$_2$ | |
| 9 | CH$_3$ | CH$_3$ | C$_6$H$_5$ | O | |
| 10 | H | H | 2-Cl—C$_6$H$_4$ | CH$_2$ | |
| 11 | H | H | 2-Cl—C$_6$H$_4$ | O | |
| 12 | CH$_3$ | CH$_3$ | 2-Cl—C$_6$H$_4$ | CH$_2$ | |
| 13 | CH$_3$ | CH$_3$ | 2-Cl—C$_6$H$_4$ | O | |
| 14 | H | H | 4-Cl—C$_6$H$_4$ | CH$_2$ | |
| 15 | H | H | 4-Cl—C$_6$H$_4$ | O | |
| 16 | CH$_3$ | CH$_3$ | 4-Cl—C$_6$H$_4$ | CH$_2$ | |
| 17 | CH$_3$ | CH$_3$ | 4-Cl—C$_6$H$_4$ | O | |
| 18 | H | H | 2,4-Cl$_2$—C$_6$H$_3$ | CH$_2$ | |
| 19 | H | H | 2,4-Cl$_2$—C$_6$H$_3$ | O | 2.81 (dd), 4.14 (s) |
| 20 | CH$_3$ | CH$_3$ | 2,4-Cl$_2$—C$_6$H$_3$ | CH$_2$ | |
| 21 | CH$_3$ | CH$_3$ | 2,4-Cl$_2$—C$_6$H$_3$ | O | |
| 22 | H | H | 2-F—C$_6$H$_4$ | CH$_2$ | |
| 23 | H | H | 2-F—C$_6$H$_4$ | O | |
| 24 | CH$_3$ | CH$_3$ | 2-F—C$_6$H$_4$ | CH$_2$ | |
| 25 | CH$_3$ | CH$_3$ | 2-F—C$_6$H$_4$ | O | |
| 26 | H | H | 4-F—C$_6$H$_4$ | CH$_2$ | |
| 27 | H | H | 4-F—C$_6$H$_4$ | O | |
| 28 | CH$_3$ | CH$_3$ | 4-F—C$_6$H$_4$ | CH$_2$ | |
| 29 | CH$_3$ | CH$_3$ | 4-F—C$_6$H$_4$ | O | 2.91 (dd); 3.86; 4.04 (2s) |
| 30 | H | H | 2-CH$_3$—C$_6$H$_4$ | CH$_2$ | |
| 31 | H | H | 2-CH$_3$—C$_6$H$_4$ | O | |
| 32 | CH$_3$ | CH$_3$ | 2-CH$_3$—C$_6$H$_4$ | CH$_2$ | |
| 33 | CH$_3$ | CH$_3$ | 2-CH$_3$—C$_6$H$_4$ | O | |
| 34 | H | H | 4-CH$_3$—C$_6$H$_4$ | CH$_2$ | |
| 35 | H | H | 4-CH$_3$—C$_6$H$_4$ | O | |
| 36 | CH$_3$ | CH$_3$ | 4-CH$_3$—C$_6$H$_4$ | CH$_2$ | |
| 37 | CH$_3$ | CH$_3$ | 4-CH$_3$—C$_6$H$_4$ | O | |
| 38 | H | H | 2-OCH$_3$—C$_6$H$_4$ | O | |
| 39 | H | H | 2-OCH$_3$—C$_6$H$_4$ | CH$_2$ | 2.44–2.80 (m); 3.82 3.83 (2s) |
| 40 | CH$_3$ | CH$_3$ | 2-OCH$_3$—C$_6$H$_4$ | O | |
| 41 | CH$_3$ | CH$_3$ | 2-OCH$_3$—C$_6$H$_4$ | CH$_2$ | |
| 42 | H | H | 2-Furyl | CH$_2$ | |
| 43 | H | H | 2-Furyl | O | |
| 44 | CH$_3$ | CH$_3$ | 2-Furyl | CH$_2$ | |
| 45 | CH$_3$ | CH$_3$ | 2-Furyl | O | |
| 46 | H | H | 2-Thienyl | O | |
| 47 | H | H | 2-Thienyl | CH$_2$ | |
| 48 | CH$_3$ | CH$_3$ | 2-Thienyl | O | |

TABLE 1-continued

| Ex | A | R | D | Z | $^1$H-NMR/Melting point |
|---|---|---|---|---|---|
| 49 | H | H | 3-Pyridyl | CH$_2$ | |
| 50 | H | H | 3-Pyridyl | O | |
| 51 | CH$_3$ | CH$_3$ | 3-Pyridyl | CH$_2$ | |
| 52 | CH$_3$ | CH$_3$ | 3-Pyridyl | O | |
| 53 | H | H | tert.-C$_4$H$_9$ | CH$_2$ | |
| 54 | H | H | tert.-C$_4$H$_9$ | O | |
| 55 | CH$_3$ | CH$_3$ | tert.-C$_4$H$_9$ | CH$_2$ | |
| 56 | CH$_3$ | CH$_3$ | tert.-C$_4$H$_9$ | O | |
| 57 | H | H | Cyclohexyl | CH$_2$ | |
| 58 | H | H | Cyclohexyl | O | |
| 59 | CH$_3$ | CH$_3$ | Cyclohexyl | CH$_2$ | |
| 60 | CH$_3$ | CH$_3$ | Cyclohexyl | O | |

TABLE 2

| Ex | A | R | D | Z | X | Melting point/IR |
|---|---|---|---|---|---|---|
| 1.1 | H | H | 4-CF$_3$—C$_6$H$_4$ | CH$_2$ | N | 120–126° C. |
| 1.2 | H | H | 4-CF$_3$—C$_6$H$_4$ | O | N | |
| 1.3 | CH$_3$ | CH$_3$ | 4-CF$_3$—C$_6$H$_4$ | CH$_2$ | N | |
| 1.4 | CH$_3$ | CH$_3$ | 4-CF$_3$—C$_6$H$_4$ | O | N | |
| 1.5 | H | H | C$_6$H$_5$ | CH$_2$ | N | |
| 1.6 | H | H | C$_6$H$_5$ | O | N | |
| 1.7 | CH$_3$ | H | C$_6$H$_5$ | CH$_2$ | N | |
| 1.8 | CH$_3$ | H | C$_6$H$_5$ | O | N | |
| 1.9 | CH$_3$ | CH$_3$ | C$_6$H$_5$ | CH$_2$ | N | |
| 1.10 | CH$_3$ | CH$_3$ | C$_6$H$_5$ | O | N | |
| 1.11 | H | tert.-C$_4$H$_9$ | C$_6$H$_5$ | O | N | |
| 1.12 | H | H | 2-Cl—C$_6$H$_4$ | CH$_2$ | N | |
| 1.13 | H | H | 2-Cl—C$_6$H$_4$ | O | N | |
| 1.14 | CH$_3$ | CH$_3$ | 2-Cl—C$_6$H$_4$ | CH$_2$ | N | |
| 1.15 | CH$_3$ | CH$_3$ | 2-Cl—C$_6$H$_4$ | O | N | |
| 1.16 | CH$_3$ | CH$_3$ | 2-Cl—C$_6$H$_4$ | CH$_2$ | CH | |
| 1.17 | CH$_3$ | CH$_3$ | 2-Cl—C$_6$H$_4$ | O | CH | |
| 1.18 | H | H | 4-Cl—C$_6$H$_4$ | CH$_2$ | N | |
| 1.19 | H | H | 4-Cl—C$_6$H$_4$ | O | N | |
| 1.20 | H | H | 4-Cl—C$_6$H$_4$ | CH$_2$ | CH | |
| 1.21 | H | H | 4-Cl—C$_6$H$_4$ | O | CH | |
| 1.22 | CH$_3$ | H | 4-Cl—C$_6$H$_4$ | CH$_2$ | N | |
| 1.23 | CH$_3$ | H | 4-Cl—C$_6$H$_4$ | O | N | |
| 1.24 | CH$_3$ | CH$_3$ | 4-Cl—C$_6$H$_4$ | O | N | |
| 1.25 | CH$_3$ | CH$_3$ | 4-Cl—C$_6$H$_4$ | CH$_2$ | N | |
| 1.26 | CH$_3$ | CH$_3$ | 4-Cl—C$_6$H$_4$ | O | CH | |
| 1.27 | CH$_3$ | CH$_3$ | 4-Cl—C$_6$H$_4$ | CH$_2$ | CH | |
| 1.28 | H | C$_2$H$_5$ | 4-Cl—C$_6$H$_4$ | O | N | |
| 1.29 | H | C$_3$H$_7$ | 4-Cl—C$_6$H$_4$ | O | N | |
| 1.30 | H | iso-C$_3$H$_7$ | 4-Cl—C$_6$H$_4$ | O | N | |
| 1.31 | H | H | 2,4-Cl$_2$—C$_6$H$_3$ | CH$_2$ | N | |
| 1.32 | H | H | 2,4-Cl$_2$—C$_6$H$_3$ | O | N | 206–212° C. |
| 1.33 | H | H | 2,4-Cl$_2$—C$_6$H$_3$ | CH$_2$ | CH | |
| 1.34 | H | H | 2,4-Cl$_2$—C$_6$H$_3$ | O | CH | >250° C. |
| 1.35 | CH$_3$ | H | 2,4-Cl$_2$—C$_6$H$_3$ | CH$_2$ | N | |
| 1.36 | CH$_3$ | H | 2,4-Cl$_2$—C$_6$H$_3$ | O | N | |
| 1.37 | CH$_3$ | CH$_3$ | 2,4-Cl$_2$—C$_6$H$_3$ | CH$_2$ | N | |
| 1.38 | CH$_3$ | CH$_3$ | 2,4-Cl$_2$—C$_6$H$_3$ | O | N | |

TABLE 2-continued structure: N=X substituted imidazole/triazole with CH2-N, cyclohexane ring with R, A, OH, Z-D substituents

| Ex | A | R | D | Z | X | Melting point/IR |
|---|---|---|---|---|---|---|
| 1.39 | H | H | 2-F—C$_6$H$_4$ | CH$_2$ | N | |
| 1.40 | H | H | 2-F—C$_6$H$_4$ | O | N | |
| 1.41 | CH$_3$ | H | 2-F—C$_6$H$_4$ | CH$_2$ | N | |
| 1.42 | CH$_3$ | H | 2-F—C$_6$H$_4$ | O | N | |
| 1.43 | CH$_3$ | CH$_3$ | 2-F—C$_6$H$_4$ | CH$_2$ | N | |
| 1.44 | CH$_3$ | CH$_3$ | 2-F—C$_6$H$_4$ | O | N | |
| 1.45 | H | H | 4-F—C$_6$H$_4$ | CH$_2$ | N | |
| 1.46 | H | H | 4-F—C$_6$H$_4$ | O | N | |
| 1.47 | H | H | 4-F—C$_6$H$_4$ | CH$_2$ | CH | |
| 1.48 | H | H | 4-F—C$_6$H$_4$ | O | CH | |
| 1.49 | CH$_3$ | H | 4-F—C$_6$H$_4$ | CH$_2$ | N | |
| 1.50 | CH$_3$ | H | 4-F—C$_6$H$_4$ | O | N | |
| 1.51 | CH$_3$ | CH$_3$ | 4-F—C$_6$H$_4$ | CH$_2$ | N | |
| 1.52 | CH$_3$ | CH$_3$ | 4-F—C$_6$H$_4$ | O | N | 2941, 1512, 1276, 1224 cm$^{-1}$ |
| 1.53 | CH$_3$ | CH$_3$ | 4-F—C$_6$H$_4$ | CH$_2$ | CH | |
| 1.54 | CH$_3$ | CH$_3$ | 4-F—C$_6$H$_4$ | O | CH | |
| 1.55 | H | C$_2$H$_5$ | 4-F—C$_6$H$_4$ | O | N | |
| 1.56 | H | C$_3$H$_7$ | 4-F—C$_6$H$_4$ | O | N | |
| 1.57 | H | C$_4$H$_9$ | 4-F—C$_6$H$_4$ | O | N | |
| 1.58 | H | C$_5$H$_{11}$ | 4-F—C$_6$H$_4$ | O | N | |
| 1.59 | H | C$_6$H$_{13}$ | 4-F—C$_6$H$_4$ | O | N | |
| 1.60 | H | H | 2-Br—C$_6$H$_4$ | CH$_2$ | N | |
| 1.61 | H | H | 2-Br—C$_6$H$_4$ | O | N | |
| 1.62 | CH$_3$ | CH$_3$ | 2-Br—C$_6$H$_4$ | CH$_2$ | N | |
| 1.63 | CH$_3$ | CH$_3$ | 2-Br—C$_6$H$_4$ | O | N | |
| 1.64 | H | H | 4-Br—C$_6$H$_4$ | CH$_2$ | N | |
| 1.65 | H | H | 4-Br—C$_6$H$_4$ | O | N | |
| 1.66 | CH$_3$ | H | 4-Br—C$_6$H$_4$ | CH$_2$ | N | |
| 1.67 | CH$_3$ | CH$_3$ | 4-Br—C$_6$H$_4$ | O | N | |
| 1.68 | H | H | 2-CH$_3$—C$_6$H$_4$ | CH$_2$ | N | |
| 1.69 | H | H | 2-CH$_3$—C$_6$H$_4$ | O | N | |
| 1.70 | CH$_3$ | CH$_3$ | 2-CH$_3$—C$_6$H$_4$ | CH$_2$ | N | |
| 1.71 | CH$_3$ | CH$_3$ | 2-CH$_3$—C$_6$H$_4$ | O | N | |
| 1.72 | H | H | 4-CH$_3$—C$_6$H$_4$ | CH$_2$ | N | |
| 1.73 | H | H | 4-CH$_3$—C$_6$H$_4$ | O | N | |
| 1.74 | CH$_3$ | CH$_3$ | 4-CH$_3$—C$_6$H$_4$ | CH$_2$ | N | |
| 1.75 | CH$_3$ | CH$_3$ | 4-CH$_3$—C$_6$H$_4$ | O | N | |
| 1.76 | H | H | 2-CF$_3$—C$_6$H$_4$ | CH$_2$ | N | |
| 1.77 | H | H | 2-CF$_3$—C$_6$H$_4$ | O | N | |
| 1.78 | CH$_3$ | CH$_3$ | 2-CF$_3$—C$_6$H$_4$ | CH$_2$ | N | |
| 1.79 | CH$_3$ | CH$_3$ | 2-CF$_3$—C$_6$H$_4$ | O | N | |
| 1.80 | H | H | 2-OCH$_3$—C$_6$H$_4$ | CH$_2$ | N | 169–173° C. |
| 1.81 | H | H | 2-OCH$_3$—C$_6$H$_4$ | O | N | |
| 1.82 | H | H | 2-OCH$_3$—C$_6$H$_4$ | CH$_2$ | CH | 142–145° C. |
| 1.83 | H | H | 2-OCH$_3$—C$_6$H$_4$ | O | CH | |
| 1.84 | CH$_3$ | CH$_3$ | 2-OCH$_3$—C$_6$H$_4$ | CH$_2$ | N | |
| 1.85 | CH$_3$ | CH$_3$ | 2-OCH$_3$—C$_6$H$_4$ | O | N | |
| 1.86 | H | H | 4-OCH$_3$—C$_6$H$_4$ | CH$_2$ | N | |
| 1.87 | H | H | 4-OCH$_3$—C$_6$H$_4$ | O | N | |
| 1.88 | CH$_3$ | CH$_3$ | 4-OCH$_3$—C$_6$H$_4$ | CH$_2$ | N | |
| 1.89 | CH$_3$ | CH$_3$ | 4-OCH$_3$—C$_6$H$_4$ | O | N | |
| 1.90 | H | H | 3-NO$_2$—C$_6$H$_4$ | CH$_2$ | N | |
| 1.91 | H | H | 3-NO$_2$—C$_6$H$_4$ | O | N | |
| 1.92 | H | H | 3-NH$_2$—C$_6$H$_4$ | CH$_2$ | N | |
| 1.93 | H | H | 3-NH$_2$—C$_6$H$_4$ | O | N | |
| 1.94 | H | H | C$_6$H$_5$—O—C$_6$H$_4$ | CH$_2$ | N | |
| 1.95 | H | H | C$_6$H$_5$—O—C$_6$H$_4$ | O | N | |
| 1.96 | H | H | 1-Naphthyl | CH$_2$ | N | |
| 1.97 | H | H | 1-Naphthyl | O | N | |
| 1.98 | H | H | 2-Naphthyl | CH$_2$ | N | |
| 1.99 | H | H | 2-Naphthyl | O | N | |
| 1.100 | CH$_3$ | CH$_3$ | 2-Naphthyl | O | N | |
| 1.101 | CH$_3$ | CH$_3$ | 2-Naphthyl | CH$_2$ | N | |
| 1.102 | H | H | 4-Biphenylyl | CH$_2$ | N | |
| 1.103 | H | H | 4-Biphenylyl | O | N | |
| 1.104 | CH$_3$ | CH$_3$ | 4-Biphenylyl | CH$_2$ | N | |
| 1.105 | CH$_3$ | CH$_3$ | 4-Biphenylyl | O | N | |
| 1.106 | H | H | tert.-C$_4$H$_9$ | CH$_2$ | N | |
| 1.107 | H | H | tert.-C$_4$H$_9$ | O | N | |
| 1.108 | CH$_3$ | CH$_3$ | tert.-C$_4$H$_9$ | CH$_2$ | N | |
| 1.109 | CH$_3$ | CH$_3$ | tert.-C$_4$H$_9$ | O | N | |
| 1.110 | H | H | 3-Cyclohexenyl | CH$_2$ | N | |
| 1.111 | H | H | 3-Cyclohexenyl | O | N | |
| 1.112 | CH$_3$ | CH$_3$ | 3-Cyclohexenyl | CH$_2$ | N | |
| 1.113 | CH$_3$ | CH$_3$ | 3-Cyclohexenyl | O | N | |
| 1.114 | H | H | Cyclopentyl | O | N | |
| 1.115 | H | H | Cyclopentyl | CH$_2$ | N | |
| 1.116 | CH$_3$ | CH$_3$ | Cyclopentyl | O | N | |
| 1.117 | CH$_3$ | CH$_3$ | Cyclopentyl | CH$_2$ | N | |
| 1.118 | CH$_3$ | CH$_3$ | Cyclopentyl | O | CH | |
| 1.119 | CH$_3$ | CH$_3$ | Cyclopentyl | CH$_2$ | CH | |
| 1.120 | H | H | Cyclohexyl | O | N | |
| 1.121 | H | H | Cyclohexyl | CH$_2$ | N | |
| 1.122 | H | H | Cyclohexyl | O | CH | |
| 1.123 | H | H | Cyclohexyl | CH$_2$ | CH | |
| 1.124 | CH$_3$ | CH$_3$ | Cyclohexyl | O | N | |
| 1.125 | CH$_3$ | CH$_3$ | Cyclohexyl | CH$_2$ | N | |

The novel fungicidal compounds or the agents containing them can be applied, for example, in the form of directly sprayable solutions, powders, suspensions, including high-percentage aqueous, oily or other suspensions or dispersions, emulsions, oil dispersions, pastes, dusting or broadcasting agents or granules by spraying, atomizing, dusting, broadcasting or watering. The application forms depend on the purposes for which they are used; they ought in every case to ensure the finest possible distribution of the active ingredients according to the invention.

Normally, the plants are sprayed or dusted with the active ingredients, or the seeds of the plants are treated with the active ingredients.

The formulations are prepared in a conventional manner, e.g. by extending the active ingredient with solvents and/or carriers, if required using emulsifiers and dispersants, it also being possible to use other organic solvents when water is used as diluent. Suitable auxiliaries for this purpose are essentially: solvents such as aromatic compounds (e.g. xylene), chlorinated aromatic compounds (e.g. chlorobenzenes), paraffins (e.g. petroleum oil fractions), alcohols (e.g. methanol, butanol), ketones (e.g. cyclohexanone), amines (e.g. ethanolamine), dimethylformamide and water; carriers such as natural rock powders (e.g. kaolins, aluminas, talc, chalks) and synthetic rock powders (e.g. highly disperse silica, silicates); emulsifiers such as non-ionic and anionic emulsifiers (e.g. polyoxyethylene fatty alcohol ethers, alkylsulfonates and arylsulfonates) and dispersants such as lignin-sulfite waste liquors and methylcellulose.

Suitable surfactants are the alkali metal, alkaline earth metal and ammonium salts of aromatic sulfonic acids, e.g. lignin-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, and of fatty alcohol glycol ethers, products of the condensation of sulfonated naphthalene and its derivatives with formaldehyde, products of the condensation of naphthalene or naphthalenesulfonic acids with phenol and formaldehyde, polyoxyethylene octylphenol ether, ethoxylated isooctyl-, octyl- or nonylphenol, alkylphenol and tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, lignin-sulfite waste liquors or methylcellulose.

Powders and dusting and broadcasting agents can be prepared by mixing or grinding the active substances together with a solid carrier.

Granules, e.g. coated, impregnated or homogeneous granules, can be prepared by binding the active ingredients to solid carriers. Examples of solid carriers are mineral earths such as silica gel, silicic acids, silicates, talc, kaolin, limestone, lime, chalk, bole, loess, clay, dolomite, diatomaceous earth, calcium and magnesium sulfates, magnesium oxide, ground plastics, fertilizers such as ammonium sulfate, ammonium phosphate, ammonium nitrate, ureas and vegetable products such as cereals flour, bark meal, wood meal and nutshell meal, cellulose powders or other solid carriers.

Examples of such formulations are:

I. a solution of 90 parts by weight of compound No. 1.1 and 10 parts by weight of N-methyl-α-pyrrolidone which is suitable for use in the form of very small drops;

II. A mixture composed of 20 parts by weight of compound No. 1..32, 80 parts by weight of xylene, 10 parts by weight of the adduct of 8 to 10 moles of ethylene oxide and 1 mole of oleic acid N-monoethanolamide, 5 parts by weight of calcium dodecylbenzenesulfonate, 5 parts by weight of the adduct of 40 moles of ethylene oxide and 1 mole of castor oil; a fine dispersion of the solution in water is used;

III. an aqueous dispersion of 20 parts by weight of compound No. 1.34, 40 parts by weight of cyclohexanone, 30 parts by weight of isobutanol, 20 parts by weight of the adduct of 40 moles of ethylene oxide and 1 mole of castor oil;

IV. an aqueous dispersion of 20 parts by weight of compound No. 1.52, 25 parts by weight of cyclohexanol, 65 parts by weight of a mineral oil fraction of boiling point 210° to 280° C. and 10 parts by weight of the adduct of 40 moles of ethylene oxide and 1 mole of castor oil;

V. 80 parts by weight of compound No. 1.80, are mixed and ground in a hammer mill, with 3 parts by weight of sodium diisobutylnaphthalene-α-sulfonate, 10 parts by weight of the sodium salt of a ligninsulfonic acid from a sulfite waste liquor and 7 parts by weight of powdered silica gel; a fine dispersion of this mixture in water can be used for spraying;

VI. an intimate mixture of 3 parts by weight of compound No. 1.82 and 97 parts by weight of finely divided kaolin; this dusting agent contains 3% by weight of active ingredient;

VII. an intimate mixture of 30 parts by weight of compound No. 1.1, 92 parts by weight of powdered silica gel and 8 parts by weight of liquid paraffin which was sprayed onto the surface of this silica gel; this formulation confers good adhesion on the active ingredient;

VIII. a stable aqueous dispersion of 40 parts by weight of compound No. 1.32, 10 parts by weight of the sodium salt of a phenolsulfonic acid/urea/formaldehyde condensate, 2 parts by weight of silica gel and 48 parts by weight of water, which can be further diluted;

IX. a stable oily dispersion of 20 parts by weight of compound No. 1.34, 2 parts by weight of calcium dodecylbenzenesulfonate, 8 parts by weight of fatty alcohol polyglycol ether, 20 parts by weight of the sodium salt of a phenolsulfonic acid/urea/formaldehyde condensate and 68 parts by weight of a liquid paraffin.

The novel compounds have excellent activity on a wide spectrum of phytopathogenic fungi, especially from the classes of Ascomycetes and Basidiomycetes. Some of them have systemic activity and can be employed as leaf- and soil fungicides.

They are particularly important for controlling a large number of fungi on various crops such as wheat, rye, barley, oats, rice, corn, grass, cotton, soybean, coffee, sugar cane, grapevines, fruit and ornamental plants and vegetables such as cucumbers, beans and pumpkins, as well as on the seeds of these plants.

The compounds are applied by treating the fungi or the seeds, plants or materials to be protected from fungal attack, or the soil, with a fungicidal amount of the active ingredients.

Application is carried out before or after infection of the materials, plants or seeds by the fungi.

The compounds I are specifically suitable for controlling the following plant diseases:

Erysiphe graminis (powdery mildew) in cereals,
Erysiphe cichoracearum and Sphaerotheca fuliginea on pumpkins,
Podosphaera leucotricha on apples,
Uncinula necator on grapevines,
Puccinia species on cereals,
Rhizoctonia species on cotton and lawns,
Ustilago species on cereals and sugar cane#
Venturia inaequalis (scab) on apples,
Helminthosporium species on cereals,
Septoria nodorum on wheat,
Botrytis cinerea (gray mold) on strawberries and grapevines,
Cercospora arachidicola on peanuts,
Pseudocercosporella herpotrichoides on wheat and barley,
Pyricularia oryzae on rice,
Phytophthora infestans on potatoes and tomatoes,
Fusarium and Verticillium species on various crops,
Plasmopara viticola on grapevines,
Alternaria species on fruit and vegetables.

The novel compounds can also be employed to protect materials (wood) e.g. against Paecilomyces variotii.

The fungicidal agents generally contain from 0.1 to 95, preferably 0.5 to 90, % by weight of active ingredient.

The application rates depend on the nature of the desired effect and range from 0.02 to 3 kg of active ingredient per ha.

The amounts of active ingredient required for seed treatment are generally from 0.001 to 50 g, preferably 0.01 to 10 g, per kilograin of seeds.

The fungicidal agents according to the invention can also contain other active ingredients, e.g. herbicides, insecticides, growth regulators, fungicides or even fertilizers.

USE EXAMPLES

The comparison substance used was E-1-[1-(4-chlorophenyl)-1-hydroxy-2-(1,2,4-triazol-1-yl)-1-ethyl]-2-phenylcyclopropane (A) which is disclosed in EP 212,605.

USE EXAMPLE 1

Activity against Pyricularia oryzae (protective)

Leaves of pot-grown rice seedlings of the "Bahia" variety were sprayed to run off with aqueous emulsions which contained (dry basis) 80% active ingredient and 20% emulsifier and, 24 hours later, inoculated with an aqueous suspension of Pyricularia oryzae spores. The test plants were then placed in climatic cabinets at 22° to 24° C. and 95 to 99% relative humidity. After 6 days the extent of infestation was determined.

The result of the test shows that active ingredients No. 1.52 and 1.81 when used as an aqueous dispersion containing 500 ppm active ingredient have a better fungicidal action (90%) than the known comparison active ingredient A (50%).

USE EXAMPLE 2

Activity against Botrytis cinerea

Paprika seedlings of the "Neusiedler Ideal Elite" variety were, after 4 or 5 leaves had developed well, sprayed to run off with aqueous suspensions which contained (dry basis) 80% active ingredient and 20% emulsifier. After the spraying had dried on, the plants were sprayed with a suspension of conidia of the fungus Botrytis cinerea and placed in a chamber at 22° to 24° C. with high humidity. After 5 days the disease had developed on the untreated control plants so greatly that the resulting leaf necroses covered most of the leaves.

The result of the test shows that active ingredient 1.52 when used as an aqueous dispersion containing 500 ppm active ingredient has a better fungicidal action (95%) than the known comparison active ingredient A (40%).

We claim:

1. An azolylmethylspiro[2.5]octanol of the formula I

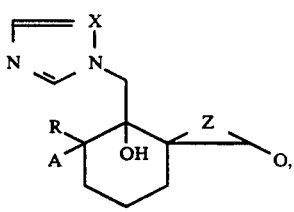

where

A and R are each hydrogen or $C_1$-$C_4$-alkyl;

D is $C_1$-$C_8$-alkyl, $C_3$-$C_6$-cycloalkyl, $C_5$-$C_8$-cycloalkenyl, biphenylyl, naphthyl, or phenyl, each of these radicals optionally substituted with one to three halogen, nitro, phenoxy, amino, $C_1$-$C_4$-alkyl, $C_1$-$C_4$-alkoxy or $C_1$-$C_4$-haloalkyl;

Z is $CH_2$ or O, and

X is N, or the plant-compatible acid addition salts or metal complexes thereof.

2. An azolylmethylspiro[2.5]octanol of the formula I as claimed in claim 1, where D is phenyl which is unsubstituted or substituted with one to three fluorine or chlorine.

3. A fungicidal composition comprising a carrier and a fungicidal amount of an azolylmethylspiro[2.5]octanol of the formula I

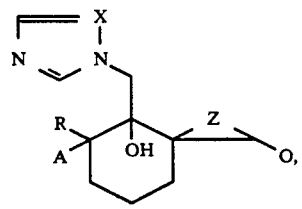

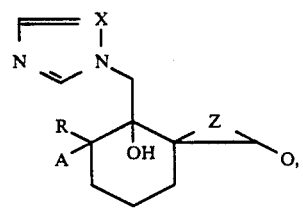

where

A and R are each hydrogen or $C_1$-$C_4$-alkyl;

D is $C_1$-$C_8$-alkyl, $C_3$-$C_6$-cycloalkyl, $C_5$-$C_8$-cycloalkenyl, biphenylyl, naphthyl, or phenyl, each of these radicals optionally substituted with one to three halogen, nitro, phenoxy, amino, $C_1$-$C_4$-alkyl, $C_1$-$C_4$-alkoxy or $C_1$-$C_4$-haloalkyl;

Z is $CH_2$ or O, and

X is N, or the plant-compatible acid addition salt or metal complex thereof.

4. A process for controlling fungi, which comprises exposing fungi or plant materials, areas, of oil plants or seeds threatened by fungal attack to a fungicidally effective amount of an azolylmethylspiro[2.5]octanol of the formula I

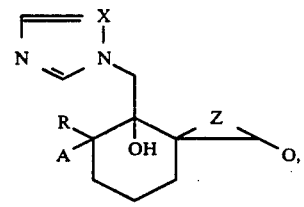

where

A and R are each hydrogen or $C_1$-$C_4$-alkyl;

D is $C_1$-$C_8$-alkyl, $C_3$-$C_6$-cycloalkyl, $C_5$-$C_8$-cycloalkenyl, biphenylyl, naphthyl, or phenyl, each of these radicals optionally substituted with one to three halogen, nitro, phenoxy, amino, $C_1$-$C_4$-alkyl $C_1$-$C_4$-alkoxy or $C_1$-$C_4$-haloalkyl;

Z is $CH_2$ or O, and

X is N, or the plant-compatible acid addition salt or metal complex thereof.

5. 4-(1,2,4-Triazol-1-ylmethyl)-4-hydroxy-1-(4-trifluoromethylphenyl)spiro[2.5]octane.

* * * * *